United States Patent
Kawakami et al.

(10) Patent No.: US 9,611,568 B2
(45) Date of Patent: Apr. 4, 2017

(54) CRIMPED CONJUGATED FIBER AND NON-WOVEN FABRIC COMPRISING THE FIBER

(75) Inventors: Yoshihisa Kawakami, Yokkaichi (JP); Kenichi Suzuki, Ichihara (JP); Yoshihiko Tomita, Sodegaura (JP)

(73) Assignee: MITSUI CHEMICALS, INC., Tokyo (JP)

( * ) Notice: Subject to any disclaimer, the term of this patent is extended or adjusted under 35 U.S.C. 154(b) by 258 days.

(21) Appl. No.: 14/114,816

(22) PCT Filed: May 10, 2012

(86) PCT No.: PCT/JP2012/061977
§ 371 (c)(1),
(2), (4) Date: Oct. 30, 2013

(87) PCT Pub. No.: WO2012/153802
PCT Pub. Date: Nov. 15, 2012

(65) Prior Publication Data
US 2014/0066873 A1    Mar. 6, 2014

(30) Foreign Application Priority Data
May 11, 2011    (JP) ................................ 2011-106100

(51) Int. Cl.
*A61F 13/53* (2006.01)
*D01F 8/06* (2006.01)
(Continued)

(52) U.S. Cl.
CPC .......... *D01F 8/06* (2013.01); *A61F 13/51121* (2013.01); *A61F 13/51401* (2013.01);
(Continued)

(58) Field of Classification Search
CPC ........ A61F 13/5116; A61F 2013/51002; A61F 2013/51009; A61F 2013/51023;
(Continued)

(56) References Cited

U.S. PATENT DOCUMENTS

| 3,904,730 A | 9/1975 | Shimizu et al. |
| 5,804,517 A | 9/1998 | Ishii et al. |

(Continued)

FOREIGN PATENT DOCUMENTS

| CN | 1168424 A | 12/1997 |
| CN | 1842620 A | 10/2006 |

(Continued)

OTHER PUBLICATIONS

Extended European Search Report dated Sep. 12, 2014, issued by the European Patent Office in the corresponding European Application No. 12782262.5. (7 pages).
(Continued)

*Primary Examiner* — Lynne Anderson
(74) *Attorney, Agent, or Firm* — Buchanan, Ingersoll & Rooney PC

(57) ABSTRACT

It is an object of the present invention to obtain crimped conjugated fibers having excellent crimp properties. The present invention provides a crimped conjugated fiber having a crimpable cross-sectional configuration, wherein a cross section of the fiber includes at least two portions: a portion (a) and a portion (b); the portion (a) includes an olefin polymer (A) and the portion (b) includes an olefin polymer (B); the olefin polymer (A) differs from the olefin polymer (B) in at least any one of Mz/Mw, melting point and MFR; and a specific fatty acid amide is added to the olefin polymer (A) and/or the olefin polymer (B). The present invention also provides a non-woven fabric including said crimped conjugated fiber.

10 Claims, 2 Drawing Sheets

(51) Int. Cl.
*D04H 1/541* (2012.01)
*D01D 5/22* (2006.01)
*A61F 13/511* (2006.01)
*A61F 13/514* (2006.01)
*B32B 5/02* (2006.01)
*C08L 23/12* (2006.01)
*D01F 1/10* (2006.01)
*A61F 13/51* (2006.01)
*C08K 5/20* (2006.01)

(52) U.S. Cl.
CPC ............. *B32B 5/022* (2013.01); *C08L 23/12* (2013.01); *D01D 5/22* (2013.01); *D01F 1/10* (2013.01); *D04H 1/541* (2013.01); *A61F 2013/5108* (2013.01); *A61F 2013/51009* (2013.01); *C08K 5/20* (2013.01); *C08L 2203/12* (2013.01); *Y10T 428/2924* (2015.01); *Y10T 442/629* (2015.04)

(58) Field of Classification Search
CPC .. A61F 2013/51028; A61F 2013/51178; A61F 2013/530167; A61F 2013/53024; A61F 2013/53472; A61F 2013/5349; B32B 5/002; B32B 5/08; B32B 2262/12; Y10T 428/2929; Y10T 428/2931
See application file for complete search history.

(56) References Cited

U.S. PATENT DOCUMENTS

| | | | |
|---|---|---|---|
| 5,876,840 A | 3/1999 | Ning et al. | |
| 5,902,679 A | 5/1999 | Kojima et al. | |
| 6,090,730 A * | 7/2000 | Fujiwara | A61F 13/511 442/361 |
| 6,454,989 B1 | 9/2002 | Neely et al. | |
| 6,548,432 B1 * | 4/2003 | Hisada | D04H 1/565 442/327 |
| 7,670,677 B2 | 3/2010 | Usui et al. | |
| 8,268,444 B2 | 9/2012 | Okaya | |
| 2002/0098764 A1 | 7/2002 | Mleziva et al. | |
| 2004/0067709 A1 | 4/2004 | Kishine et al. | |
| 2007/0021022 A1 | 1/2007 | Kishine et al. | |
| 2009/0111347 A1 | 4/2009 | Peng et al. | |
| 2011/0189915 A1 | 8/2011 | Morimoto et al. | |
| 2012/0184166 A1 | 7/2012 | Kurihara et al. | |

FOREIGN PATENT DOCUMENTS

| | | |
|---|---|---|
| CN | 101522964 A | 9/2009 |
| EP | 0 833 002 A1 | 4/1998 |
| EP | 0 959 165 A1 | 11/1999 |
| EP | 1 023 473 B1 | 8/2000 |
| EP | 2 479 320 A1 | 7/2012 |
| JP | 05-263353 A | 10/1993 |
| JP | 07-197367 A | 8/1995 |
| JP | 2002-529617 A | 9/2002 |
| JP | 2007-308868 A | 11/2007 |
| WO | WO 99/28544 A1 | 6/1999 |
| WO | WO 02/061192 A1 | 8/2002 |
| WO | WO 2007/140163 A2 | 12/2007 |
| WO | WO 2007/140163 A3 | 12/2007 |
| WO | WO 2010/050407 A1 | 5/2010 |
| WO | WO 2011/034113 A1 | 3/2011 |

OTHER PUBLICATIONS

Chinese Office Action dated Jun. 25, 2014, issued by the Chinese Patent Office in corresponding Chinese Patent Application No. 201280022179.X (9 pages).

International Search Report (Form PCT/ISA/210) issued on Aug. 7, 2012, by the Japanese Patent Office as the International Searching Authority for International Application No. PCT/JP2012/061977. (5 pages).

Office Action dated Jun. 11, 2013, issued in corresponding Japanese Patent Application No. 2013-514052. (2 pages).

* cited by examiner

CRIMPED CONJUGATED FIBER AND NON-WOVEN FABRIC COMPRISING THE FIBER

TECHNICAL FIELD

The present invention relates to crimped conjugated fibers and a non-woven fabric comprising the fibers.

BACKGROUND ART

Polypropylene non-woven fabrics have excellent properties such as breathability and softness and are used as sanitary materials including disposable diapers and sanitary napkins. However, further improvements in their properties have been required. For example, polypropylene non-woven fabrics further improved in softness, bulkiness and mechanical strength are desired.

To obtain non-woven fabrics having excellent softness and bulkiness, various methods have been proposed in which non-woven fabrics are formed of crimped polypropylene fibers. For example, Patent Document 1 discloses non-woven fabrics that comprise conjugated fibers having a crimpable cross-sectional configuration wherein the conjugated fibers comprise a first component comprising propylene polymer and a second component comprising polypropylene with different physical properties from the first component. The second polypropylene is selected from the group consisting of high MFR polypropylenes, low polydispersity polypropylenes, amorphous polypropylenes and elastic (elastomeric) polypropylenes. According to the disclosure, by composite melt spinning the first component and the second component having different physical properties from each other, the resultant conjugated fibers give crimped fibers capable of forming non-woven fabrics with excellent softness and elastic properties.

Patent Document 2 discloses non-woven fabrics that comprise parallel type crimped conjugated fibers comprising ethylene/propylene random copolymer and polypropylene.

Patent Document 3 discloses non-woven fabrics that comprise crimped conjugated fibers comprising two propylene polymers of which a difference between the melting points is 20° C. or more. Patent Document 3 describes that the propylene polymers may be blended with various known additives.

In Patent Document 1, crimped conjugated fibers are obtained from a combination of polypropylenes having dissimilar properties. In detail, Example 1 discloses a combination of polypropylenes having differing MFR and molecular weight distribution in which parallel type conjugated fibers are formed from a first polypropylene having an MFR of 35 and a polydispersity number of 3 and a second polypropylene having an MFR of 25 and a polydispersity number of 2.

The conjugated fibers obtained by combining ethylene/propylene random copolymer and polypropylene that differ in crystallization rate and the crimped conjugated fibers obtained by combining two propylene polymers of which a difference between the melting points is 20° C. or more, as described in Patent Document 2 and Patent Document 3, are excellent in crimp properties. However, depending on applications, non-woven fabrics further excellent in crimp properties and bulkiness are desired.

CITATION LIST

Patent Documents

Patent Document 1: JP-A-2002-529617
Patent Document 2: JP-A-H07-197367
Patent Document 3: WO 2002/061192

SUMMARY OF THE INVENTION

Technical Problem

It is an object of the present invention to obtain conjugated fibers having crimp properties and a non-woven fabric excellent in softness, fuzzing resistance and visibility, obtained from the fibers.

Technical Solution

The present inventors studied diligently and have found that crimped fibers improved in softness and visibility while having high crimp properties, for example conjugated fibers having an eccentric core-sheath configuration, are obtained from two olefin polymers differing in physical properties such as melting point and MFR by adding a fatty acid amide having 19 or less carbon atoms to an olefin polymer used in the sheath and/or an olefin polymer used in the core. The present invention has been completed based on the finding.

In accordance with an aspect of the present invention, there is provided a crimped conjugated fiber having a crimpable cross-sectional configuration, wherein a cross section of the fiber comprises at least two portions: a portion (a) and a portion (b);

the mass ratio of the portion (a) to the portion (b) [(a):(b)] is in the range of 10:90 to 60:40;

the portion (a) comprises an olefin polymer (A) and the portion (b) comprises an olefin polymer (B);

the olefin polymer (A) differs from the olefin polymer (B) in any one of Mz/Mw, melting point and MFR; and a fatty acid amide having 19 or less carbon atoms is added to the olefin polymer (A) and/or the olefin polymer (B).

Advantageous Effect of the Invention

The crimped conjugated fibers of the present invention are capable of providing a non-woven fabric superior in bulkiness, softness, fuzzing resistance and uniformity while having high crimp properties compared with conventional crimped conjugated fibers composed of an olefin polymer. Especially, a non-woven fabric superior in visibility and uniformity is obtained by combining olefin polymers composing the crimped conjugated fibers wherein the difference between the melting points of the olefin polymers is in the range of less than 20° C.

DESCRIPTION OF EMBODIMENTS

Olefin Polymer (A)

Figure 1:
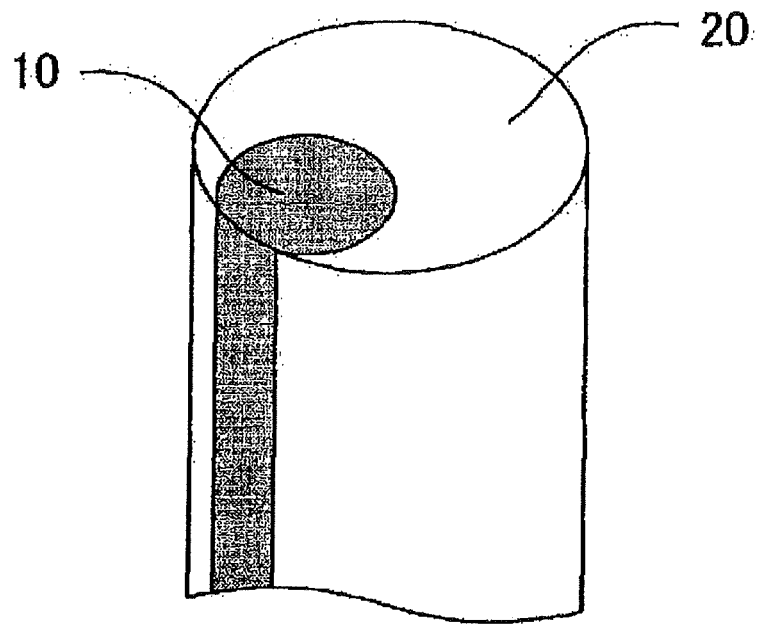
FIG. 1 is a perspective view showing an embodiment of a crimped conjugated fiber according to the present invention.
Figure 2:
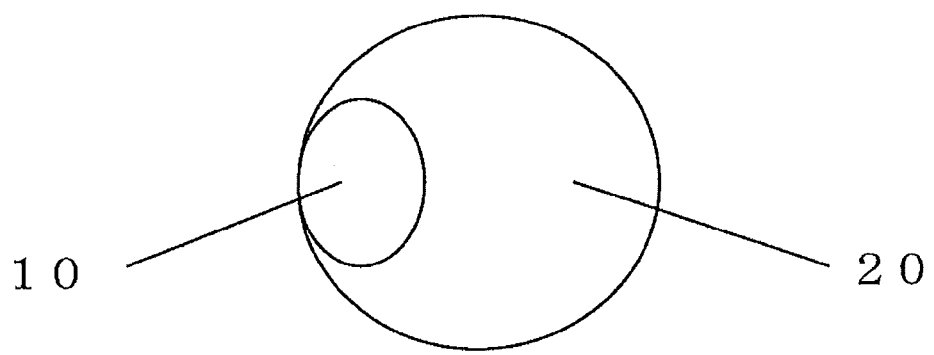
FIG. 2 is a cross-sectional view showing an embodiment of a crimped conjugated fiber according to the present invention.
Figure 3:
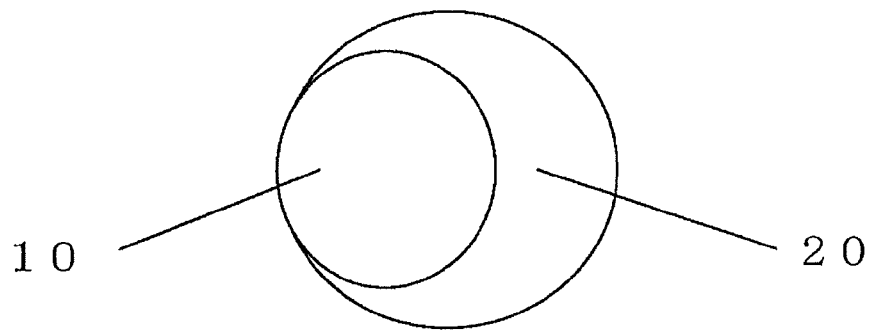
FIG. 3 is a cross-sectional view showing an embodiment of a crimped conjugated fiber according to the present invention.
Figure 4:
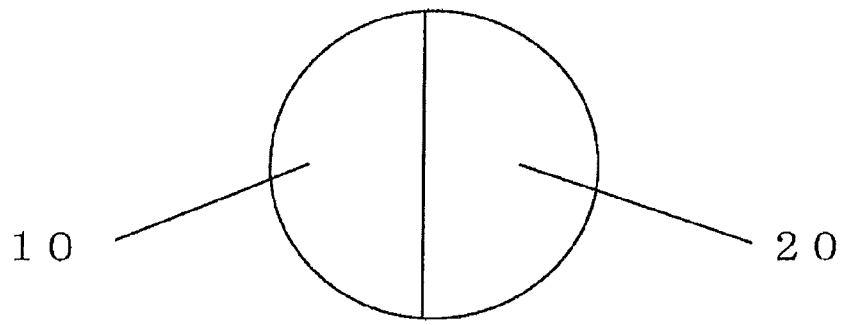
FIG. 4 is a cross-sectional view showing an embodiment of a crimped conjugated fiber according to the present invention.
Figure 5:
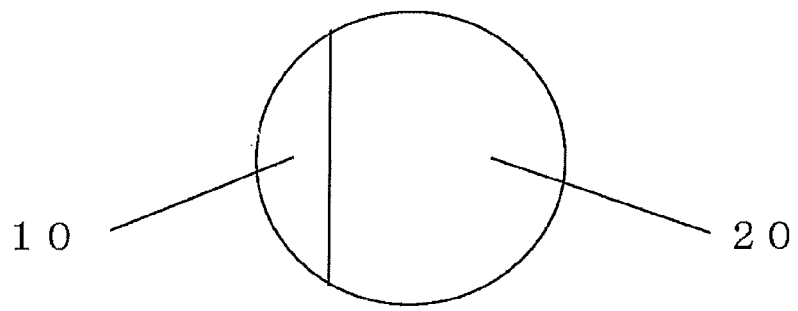
FIG. 5 is a cross-sectional view showing an embodiment of a crimped conjugated fiber according to the present invention.
Figure 6:
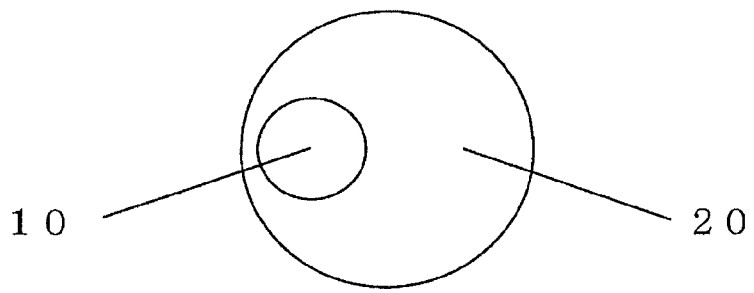
FIG. 6 is a cross-sectional view showing an embodiment of a crimped conjugated fiber according to the present invention.
Figure 7:
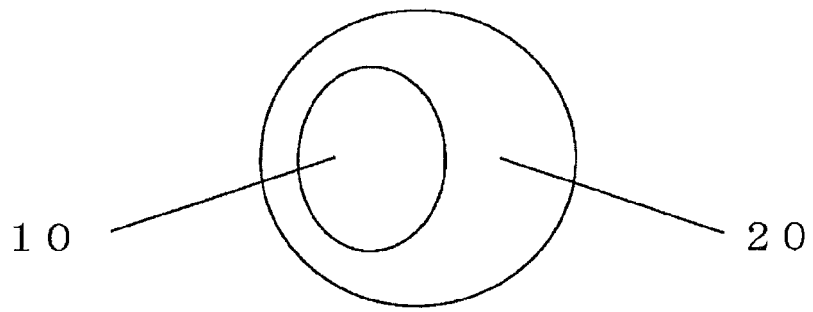
FIG. 7 is a cross-sectional view showing an embodiment of a crimped conjugated fiber according to the present invention.

In the crimped conjugated fibers of the present invention having a crimpable cross-sectional configuration wherein a cross section of the fibers comprises at least two portions: a portion (a) and a portion (b) (hereinafter may be simply referred to as "crimped conjugated fibers"), the olefin polymer (A) for forming the portion (a) is a homo- or copolymer of an α-olefin such as ethylene, propylene, 1-butene, 1-hexene, 4-methyl-1-pentene or 1-octene. Specific examples of the olefin polymer (A) are crystalline olefin polymers including: ethylene polymers such as high-pressure low-density polyethylenes, linear low-density polyethylenes (so-called LLDPEs: ethylene/α-olefin random copolymers) and high density polyethylenes; propylene polymers such as propylene homopolymers and propylene/α-olefin copolymers; 1-butene polymers such as 1-butene homopolymers and 1-butene/α-olefin copolymers; and 4-methyl-1-pentene polymers such as 4-methyl-1-pentene homopolymers and 4-methyl-1-pentene/α-olefin copolymers.

The olefin polymer (A) according to the present invention differs from the olefin polymer (B) for forming the portion (b) in the crimped conjugated fibers (hereinafter may be simply referred to as "crimped conjugated fibers") according to the present invention in at least any one of Mz/Mw, melting point and MFR.

The olefin polymer (A) according to the present invention is preferably a propylene polymer (A1) because of having high productivity and high strength.

<Propylene Polymer (A1)>

The propylene polymer (A1) for forming the portion (a) in the crimped conjugated fibers according to the present invention preferably has a ratio (Mz/Mw) of Z-average molecular weight (Mz) to weight average molecular weight (Mw) of 2.0 or more, preferably in the range of 2.1 to 4.5. The propylene polymer (A1), by having (Mz/Mw) within the above range, can be a propylene polymer having a ratio [Mz/Mw (A1)] of Z-average molecular weight (Mz) to weight average molecular weight (Mw) different from the ratio [Mz/Mw (B)] of Z-average molecular weight (Mz) to weight average molecular weight (Mw) of a propylene polymer (B1) described later.

The propylene polymer (A1) according to the present invention usually has a melting point of not lower than 120° C., preferably in the range of 125 to 165° C.

When a propylene homopolymer (A2) or a propylene/α-olefin copolymer (A3) having a melting point of 155° C. or more, more preferably in the range of 157 to 165° C., is used as the propylene polymer (A1) according to the present invention, it is easy to control the difference of the melting point between the propylene polymer (B1) described later and the propylene polymer (A1) to be 5° C. or more, more preferably 10° C. or more.

The propylene polymer (A1) according to the present invention usually has a melt flow rate (MFR) (ASTM D-1238, 230° C., 2160 g load) of 20 to 100 g/10 min, preferably 30 to 80 g/10 min. If MFR of the propylene polymer is less than 20 g/10 min, the melt viscosity is high and the spinnability is poor. If MFR of the propylene polymer exceeds 100 g/10 min, an obtainable non-woven fabric may have poor tensile strength.

The propylene polymer (A1) according to the present invention is a propylene polymer containing propylene as a main component, with examples including a propylene homopolymer and a propylene/α-olefin random copolymer having a small amount, e.g., not more than 10 mol %, of one or more kind(s) of α-olefins such as ethylene, 1-butene, 1-pentene, 1-hexene, 1-octene, 1-decene, 3-methyl-1-butene, 3-methyl-1-pentene, 3-ethyl-1-pentene, 4-methyl-1-pentene and 4-methyl-1-hexene. Examples of the propylene/α-olefin random copolymers include a propylene/ethylene random copolymer and a propylene/ethylene/1-butene random copolymer. The propylene polymer (A1) is preferably a propylene homopolymer.

The propylene polymer (A1) according to the present invention is obtained by homopolymerizing propylene or copolymerizing propylene and a small amount of α-olefin by a method of slurry polymerization, gas-phase polymerization or bulk polymerization using a Ziegler-Natta catalyst that contains a titanium-containing solid transition metal component and an organometallic component or a metallocene catalyst that contains a compound of transition metal of Groups IV to VI of the periodic table having at least one cyclopentadienyl skeleton and a cocatalyst component.

The propylene polymer (A1) according to the present invention may be blended with known additives or other polymers as required while still achieving the objects of the present invention, as well as a fatty acid amide having 19 or less carbon atoms. Exemplary additives are antioxidants, weathering stabilizers, light stabilizers, antistatic agents, anti-fogging agents, anti-blocking agents, lubricants, nucleating agents and pigments.

<Olefin Polymer (B)>

In the crimped conjugated fibers of the present invention having a crimpable cross-sectional configuration wherein a cross section of the fibers comprises at least two portions: a portion (a) and a portion (b), the olefin polymer (B) for forming the portion (b) is a crystalline olefin polymer of which the category is the same as that of the olefin polymer (A). The olefin polymer (B) differs from the olefin polymer (A) in at least any one of Mz/Mw, melting point and MFR.

The olefin polymer (B) according to the present invention is preferably a propylene polymer (B1) because of having high productivity and high strength.

<Propylene Polymer (B1)>

The propylene polymer (B1) for forming the portion (b) in the crimped conjugated fibers according to the present invention preferably has a ratio (Mz/Mw) of Z-average molecular weight (Mz) to weight average molecular weight (Mw) of 2.0 or more, preferably in the range of 2.1 to 4.5. The propylene polymer (B1), by having (Mz/Mw) within the above range, can be a propylene polymer having a ratio [Mz/Mw (B1)] of Z-average molecular weight (Mz) to weight average molecular weight (Mw) different from the ratio [Mz/Mw (A1)] of Z-average molecular weight (Mz) to weight average molecular weight (Mw) of the propylene polymer (A1).

The propylene polymer (B1) according to the present invention usually has a melting point of not lower than 120° C., preferably in the range of 125 to 165° C.

When a propylene/α-olefin copolymer (B2) preferably having a melting point of 120 to 155° C., more preferably in the range of 125 to 150° C., is used as the propylene polymer (B1) according to the present invention, it is easy to control the difference of the melting point between the propylene polymer (B1) and the propylene polymer (A1) or the propylene homopolymer (A2) to be 5° C. or more, more preferably 10° C. or more.

The propylene polymer (B1) according to the present invention usually has a melt flow rate (MFR) (ASTM D-1238, 230° C., 2160 g load) of 20 to 100 g/10 min, preferably 30 to 80 g/10 min. If MFR of the propylene polymer is less than 20 g/10 min, the melt viscosity is high and the spinnability is poor. If MFR of the propylene polymer exceeds 100 g/10 min, an obtainable non-woven fabric may have poor tensile strength.

The propylene polymer (B1) according to the present invention is a propylene homopolymer or a random copolymer of propylene with a small amount, e.g., not more than 10 mol % of an α-olefin, specifically, one or more α-olefins (excluding propylene) such as ethylene, 1-butene, 1-pentene, 1-hexene, 1-octene, 1-decene, 3-methyl-1-butene, 3-methyl-1-pentene, 3-ethyl-1-pentene, 4-methyl-1-pentene and 4-methyl-1-hexene.

The propylene polymer (B1) according to the present invention can be produced by the same polymerization method as in the case of the propylene polymer (A1).

The propylene polymer (B1) according to the present invention may be blended with known additives or other polymers as required while still achieving the objects of the present invention, as well as a fatty acid amide having 19 or less carbon atoms. Exemplary additives are antioxidants, weathering stabilizers, light stabilizers, antistatic agents, anti-fogging agents, anti-blocking agents, lubricants, nucleating agents and pigments.

<Fatty Acid Amide>

The fatty acid amide blended into the olefin polymer (A) and/or the olefin polymer (B) according to the present invention is a fatty acid amide having 19 or less, preferably 16 to 18, carbon atoms. The number of carbon atoms in such a case refers to the number of carbon atoms in a fatty acid moiety in a fatty acid amide. The fatty acid that constitutes the fatty acid amide may be a saturated fatty acid or an unsaturated fatty acid or may be a primary amide or a secondary amide. Specific examples of the fatty acid amide according to the present invention include primary amides such as palmitic acid (C16) amide, stearic acid (C18) amide and oleic acid (C18) amide and secondary amides such as N-oleylpalmitic acid (C16) amide, myristic acid amide (C13) and lauric acid amide (C11).

Of the fatty acid amides, stearic acid (C18) amide, oleic acid (C18) amide and N-oleylpalmitic acid (C16) amide are particularly preferred in terms of softness, fuzzing resistance and uniformity.

If a fatty acid amide having more than 19 carbon atoms, e.g., erucic acid (C22) amide, is used as the fatty acid amide and added to the propylene polymer, improved effects such as crimp properties, softness, fuzzing resistance and uniformity are insufficient.

<Crimped Conjugated Fiber>

The crimped conjugated fibers of the present invention have a crimpable cross-sectional configuration, wherein a cross section of the fiber comprises at least two portions: a portion (a) and a portion (b);

the mass ratio of the portion (a) to the portion (b) [(a):(b)] is in the range of 10:90 to 60:40;

the portion (a) comprises an olefin polymer (A) and the portion (b) comprises an olefin polymer (B);

the olefin polymer (A) differs from the olefin polymer (B) in at least any one of Mz/Mw, melting point and MFR; and a fatty acid amide having 19 or less carbon atoms is added to the olefin polymer (A) and/or the olefin polymer (B).

A combination of the olefin polymer (A) and the olefin polymer (B) differing in Mz/Mw from each other is such that the difference between the ratio [Mz/Mw (A)] of Z-average molecular weight (Mz) to weight average molecular weight (Mw) of the olefin polymer (A) and the ratio [Mz/Mw (B)] of Z-average molecular weight (Mz) to weight average molecular weight (Mw) of the olefin polymer (B) is preferably in the range of 0.1 to 2.2, more preferably 0.1 to 0.4.

Herein, Mz of the olefin polymer (A) or the olefin polymer (B) is known as Z-average molecular weight and is defined by Equation (1) below:

$$Mz = \frac{\sum M_i^3 N_i}{\sum M_i^2 N_i} \quad (1)$$

In Equation (1), $M_i$ is the molecular weight of the polymer (the olefin polymer (A) and the olefin polymer (B); hereinafter, referred to as the "olefin polymer" when these two polymers are combined) and $N_i$ is the number of moles of the polymer (olefin polymer).

In general, Mz is considered to reflect more precisely high-molecular weight components in a polymer. Therefore, the Mz/Mw indicates a molecular weight distribution reflecting more precisely high-molecular weight components than the usual molecular weight distribution Mw/Mn. The molecular weight distribution Mz/Mw affects fiber crimp properties.

<ΔMw/Mn>

As long as Mz/Mw of the olefin polymer (A) is different from Mz/Mw of the olefin polymer (B), an absolute value of the difference between Mw/Mn(A) of the olefin polymer (A) according to the present invention and Mw/Mn(B) of the olefin polymer (B) [Mw/Mn(A)−Mw/Mn(B):ΔMw/Mn] may be 1.5 or below, in which case obtainable conjugated fibers still have excellent crimp properties. Even when an absolute value of ΔMw/Mn is in the range of 0.3 to 1.0, crimps are developed. The ratio Mw/Mn is usually known as the molecular weight distribution (polydispersity degree) indicating the degree of molecular weight distribution of a polymer. If ΔMw/Mn is excessively large, flow properties and crystallization behaviors greatly differ between one material (the portion (a)) and another material (the portion (b)), possibly resulting in deteriorated fiber spinnability. In the present invention, the numerical ranges indicated with "to" include the numbers at the sides of the "to".

Mz/Mw and ΔMw/Mn are obtained by determining, by GPC analysis, the ratios Mz/Mw and the ratios Mw/Mn each for the olefin polymer (A) and the olefin polymer (B) that form the portion (a) and the portion (b) respectively, and calculating an absolute value of the difference thereof.

In the present invention, GPC analysis is performed under the following conditions.

(1) 30 mg of the olefin polymer is completely dissolved in 20 mL of o-dichlorobenzene at 145° C.

(2) The solution is filtered through a sintered filter having a pore size of 1.0 μm to provide a sample.

(3) The sample is analyzed by GPC and the average molecular weight and molecular weight distribution curve are obtained with reference to polystyrene (PS) standard.

The measurement apparatus and conditions are as follows.

Measurement apparatus: Gel permeation chromatograph Alliance GPC 2000 (manufactured by Waters)

Analyzer: Data processing software Empower 2 (manufactured by Waters)

Columns: Two TSK gel GMH6-HT columns+two TSK gel GMH6-HTL columns (each 7.5 mm in inner diameter× 30 cm, manufactured by TOSOH CORPORATION)

Column temperature: 140° C.

Mobile phase: o-dichlorobenzene (containing 0.025% of butylated hydroxytoluene (BHT))

Detector: Differential refractometer

Flow rate: 1 mL/min

Sample concentration: 30 mg/20 mL

Injection amount: 500 µL

Sampling time intervals: 1 sec

Column calibration: Monodisperse polystyrenes (manufactured by TOSOH CORPORATION)

Molecular weight conversion: PS conversion/standard conversion methods

The crimped conjugated fibers having excellent crimp properties can be obtained by selecting the olefin polymer (A) and the olefin polymer (B) differing in Mz/Mw, preferably having the Mz/Mw difference within the above range, even if there is no difference between the melting points or MFRs of the olefin polymer (A) and the olefin polymer (B).

As a combination of the olefin polymer (A) and the olefin polymer (B) differing in Mz/Mw, a combination of the propylene polymer (A1) and the propylene polymer (B1) is preferred because of high productivity and high strength.

As a combination of the olefin polymer (A) and the olefin polymer (B) differing in melting point from each other, preferred is a combination of the olefin polymer (A) and the olefin polymer (B) wherein the difference between their melting points is preferably 5° C. or more, more preferably more than 10° C., since the crimped conjugated fibers superior in crimp properties are provided. On the other hand, when the difference between the melting points of the olefin polymer (A) and the olefin polymer (B) exceeds 20° C., crimp properties are further improved, but a non-woven fabric resulting from such crimped conjugated fibers may have deteriorated visibility and uniformity, and therefore the difference between the melting points of the olefin polymer (A) and the olefin polymer (B) is more preferably less than 20° C.

The difference between the melting points of the olefin polymer (A) and the olefin polymer (B) is obtained by determining the melting points of the olefin polymer (A) and the olefin polymer (B) that are raw materials for the portion (a) and the portion (b) respectively and calculating an absolute value of the difference thereof.

In the present invention, the melting point is measured as follows.

(1) The olefin polymer is set in a pan of a differential scanning calorimeter (DSC) manufactured by PerkinElmer, Inc. The pan is heated from 30 to 200° C. at a rate of 10° C./min, held at 200° C. for 10 minutes, and cooled to 30° C. at a rate of 10° C./min.

(2) The pan is heated again from 30 to 200° C. at a rate of 10° C./min, and the melting point is obtained from the peak recorded during this second heating process.

The crimped conjugated fibers having excellent crimp properties can be obtained by making the difference between the melting points of the olefin polymer (A) and the olefin polymer (B) within the above range, even if there is no ΔMz/Mw or MFR difference of the olefin polymer (A) and the olefin polymer (B).

As a combination of the olefin polymer (A) and the olefin polymer (B) differing in melting point, a combination of the propylene homopolymer (A2) and the propylene/α-olefin copolymer (B2) is preferred because of high productivity and high strength.

The olefin polymer (A) and the olefin polymer (B) differing in MFR are combined so that the difference between the MFRs of the olefin polymer (A) and the olefin polymer (B) is preferably 5 or less, more preferably 3 or less.

The crimped conjugated fibers having excellent crimp properties can be obtained by making the difference between the MFRs of the olefin polymer (A) and the olefin polymer (B) within the above range, even if there is no ΔMz/Mw or melting point difference of the olefin polymer (A) and the olefin polymer (B).

The combination of the olefin polymer (A) and the olefin polymer (B) according to the present invention may be a combination of the olefin polymers differing in all of Mz/Mw, melting point and MFR.

The amount of the blended fatty acid amide is usually in the range of 0.1 to 10 parts by weight, preferably 0.1 to 3.0 parts by weight, more preferably 0.1 to 2.0 parts by weight, based on 100 parts by weight of the olefin polymer (A) and/or the olefin polymer (B). If the amount of the blended fatty acid amide is less than 0.1 part by weight, the crimp properties of the obtainable crimped conjugated fibers are insufficient. On the other hand, if the amount of the blended fatty acid amide exceeds 10 parts by weight, the effect of improving the crimp properties is saturated and the amounts of the fatty acid amide spread on the surfaces of the obtainable crimped conjugated fibers and a non-woven fabric containing the fibers is increased, so that molding processability may be deteriorated.

In an embodiment, in the crimped conjugated fibers of the present invention, the crimpable cross-sectional configuration may be an eccentric core-sheath configuration in which the core is the portion (a) formed of the olefin polymer (A) and the sheath is the portion (b) formed of the olefin polymer (B). The core formed of the portion (a) may be completely covered with the sheath of the olefin polymer (B), or part of the core may be exposed on the surface of the crimped conjugated fibers. The joint between the core and the sheath may be straight or curved. In an embodiment, the joint between the core and the sheath may be straight and part of the core may be exposed on the surface of the crimped conjugated fibers, a configuration known as a side-by-side configuration.

<Mass Ratio of the Portion (a) to the Portion (b)>

In the crimped conjugated fibers of the present invention, the mass ratio of the portion (a) to the portion (b) [(a):(b)] is in the range of 10:90 to 60:40, preferably 10:90 to 50:50, more preferably 20:80 to 40:60. If the mass ratio of the portion (a) to the portion (b) is in excess of or below the above range, the significant effect of improving crimp properties is not obtained even when the fatty acid amide is added.

<Crimp Number and Other Properties of Crimped Conjugated Fibers>

The number of crimps of the crimped conjugated fibers of the present invention is determined in accordance with JIS L 1015. The number of crimps is usually 18 or more, preferably 20 to 50, per 25 mm of the fiber, and further preferably 20 to 40, most preferably 20 to 30, from the viewpoint of the visibility and uniformity of an obtainable non-woven fabric. If the number of crimps is less than the lower limit, the crimped fibers may not achieve characteristics such as bulkiness by the three dimensional helical structure. If the number of crimps is larger than the upper limit, uniform distribution of the fibers is difficult and an obtainable non-woven fabric may have deteriorated uniformity or mechanical strength.

The diameter of the crimped conjugated fibers of the present invention is not particularly limited, but is usually in the range of 0.5 to 5 denier, preferably 0.5 to 3 denier. This fineness ensures excellent spinnability and crimp properties, and mechanical strength of an obtainable non-woven fabric comprising the crimped conjugated fibers of the present invention.

FIG. 1 is a perspective view showing an embodiment of the crimped conjugated fibers according to the present invention. In the figure, reference numeral 10 denotes the portion (a) and reference numeral 20 denotes the portion (b).

The crimped conjugated fibers of the present invention have a crimpable cross-sectional configuration wherein a cross section of the fibers comprises at least two portions: the portion (a) and the portion (b). In the cross section of the crimped conjugated fibers, the proportions of the portion (a) and the portion (b) are such that the mass ratio [(a):(b)] is in the range of 10:90 to 60:40, preferably 10:90 to 50:50, more preferably 20:80 to 40:60.

The crimped conjugated fibers may have any shapes without limitation as long as they have a crimpable cross-sectional configuration. Exemplary shapes include side-by-side (parallel) crimped conjugated fibers in which the portion (a) and the portion (b) are arranged adjacent to each other, and core-sheath crimped conjugated fibers in which the portion (a) forms a core (a') and the portion (b) forms a sheath (b').

FIGS. 2 to 7 show other cross-sectional views of crimped conjugated fibers according to the present invention. In the figures, reference numeral 10 denotes the portion (a) and reference numeral 20 denotes the portion (b).

The term "core-sheath crimped conjugated fibers" refers to fibers which have a core and a sheath and are crimped. The core (a') is arranged with at least part thereof being surrounded by a polymer different from the core (a') in the fiber cross section and extends along the length of the fiber. The sheath (b') is arranged so as to surround at least part of the core (a') in the fiber cross section and extends along the length of the fiber. In an eccentric core-sheath crimped conjugated fiber, the core (a') and the sheath (b') are located non-concentrically in the cross section of the fiber. The eccentric core-sheath crimped conjugated fibers include an exposed type in which the side of the core (a') is exposed, and a non-exposed type in which the core (a') is fully occluded. In the present invention, eccentric core-sheath crimped conjugated fibers of the exposed type are preferred because the eccentric core-sheath crimped conjugated fibers of the exposed type can exhibit excellent crimp properties. The cross sectional joint between the core (a') and the sheath (b') may be straight or curved. The core may be circular, elliptical or square in cross section.

The crimped conjugated fibers of the present invention may be staple fibers or continuous fibers. Continuous fibers are preferable because an obtainable non-woven fabric does not have loss of the crimped conjugated fibers and excellent fuzzing resistance is achieved.

<Non-Woven Fabric>

The non-woven fabric of the present invention comprises the above crimped conjugated fibers. The non-woven fabric usually has a basis weight (mass per unit area of the non-woven fabric) of 3 to 100 $g/m^2$, preferably 7 to 60 $g/m^2$.

The non-woven fabric of the present invention preferably comprises the crimped conjugated fibers that are continuous fibers. In view of productivity, the non-woven fabric is particularly preferably spunbonded non-woven fabric of such fibers.

In the non-woven fabric of the present invention, it is preferable that the crimped conjugated fibers are thermally fusion bonded by embossing, whereby the fibers maintain stability and strength.

Further, the non-woven fabric of the present invention comprises the crimped conjugated fibers, preferably crimped conjugated continuous fibers, preferably having a KOSHI value of 7.4 or less and a uniformity index (V) of 420 or less, further preferably a KOSHI value of 7.35 or less and a uniformity index (V) of 400 or less, more preferably a KOSHI value of 7.3 or less and a uniformity index (V) of 380 or less.

The non-woven fabric having KOSHI and a uniformity index (V) satisfying the above ranges is preferred because of being excellent in softness and visibility.

<Non-Woven Fabric Laminate>

The non-woven fabric comprising the crimped conjugated fibers of the present invention (hereinafter, also referred to as the "crimped conjugated fiber non-woven fabric" to be distinguished from a usual non-woven fabric) may be laminated with various layers depending on use.

In detail, the crimped conjugated fiber non-woven fabric may be laminated with knitted fabrics, woven fabrics, non-woven fabrics, films and the like. The crimped conjugated fiber non-woven fabric may be laminated (joined) with such other layers by known methods including thermal fusion bonding methods such as heat embossing and ultrasonic fusion bonding, mechanical entanglement methods such as needle punching and water jetting, adhesive bonding methods with hot melt adhesives or urethane adhesives, and extrusion laminating methods.

The non-woven fabrics laminated with the crimped conjugated fiber non-woven fabric include various known non-woven fabrics such as spunbonded non-woven fabrics, meltblown non-woven fabrics, wet non-woven fabrics, dry non-woven fabrics, dry pulp non-woven fabrics, flash-spun non-woven fabrics and spread-fiber non-woven fabrics.

The materials for such non-woven fabrics may be conventional thermoplastic resins. Examples thereof include homopolymers and copolymers of α-olefins such as ethylene, propylene, 1-butene, 1-hexene, 4-methyl-1-pentene and 1-octene, namely, polyolefins such as high-pressure low-density polyethylenes, linear low-density polyethylenes (LLDPE), high-density polyethylenes, polypropylenes, polypropylene random copolymers, poly-1-butene, poly-4-methyl-1-pentene, ethylene/propylene random copolymers, ethylene/1-butene random copolymers and propylene/1-butene random copolymers; polyesters such as polyethylene terephthalate, polybutylene terephthalate and polyethylene naphthalate; polyamides such as nylon-6, nylon-66 and polymethaxyleneadipamide; polyvinyl chloride, polyimides, ethylene/vinyl acetate copolymers, polyacrylonitriles, polycarbonates, polystyrenes, ionomers and thermoplastic polyurethanes; and mixtures of these resins. Of these, high-pressure low-density polyethylenes, linear low-density polyethylenes (LLDPE), high-density polyethylenes, polypropylenes, polypropylene random copolymers, polyethylene terephthalate and polyamides are preferred.

In a preferred embodiment of the present invention, the crimped conjugated fiber non-woven fabric is laminated with a spunbonded non-woven fabric made of an ultrafine fiber (fineness: 0.8 to 2.5 denier, more preferably 0.8 to 1.5 denier) and/or a meltblown non-woven fabric. Specific examples include: two-layer laminates such as spunbonded non-woven fabric (ultrafine fiber)/crimped conjugated fiber non-woven fabric, and meltblown non-woven fabric/crimped conjugated fiber non-woven fabric; three-layer laminates such as spunbonded non-woven fabric (ultrafine fiber)/crimped conjugated fiber non-woven fabric/spunbonded non-woven fabric (ultrafine fiber), spunbonded non-woven fabric (ultrafine fiber)/crimped conjugated fiber non-woven fabric/meltblown non-woven fabric, spunbonded non-woven fabric (ultrafine fiber)/meltblown non-woven fabric/crimped conjugated fiber non-woven fabric, crimped conjugated fiber non-woven fabric/spunbonded non-woven fabric (ultrafine fiber)/crimped conjugated fiber non-woven fabric, crimped conjugated fiber non-woven fabric/spunbonded non-woven fabric (ultrafine fiber)/meltblown non-woven fabric, and crimped conjugated fiber non-woven fabric/meltblown non-woven fabric/crimped conjugated fiber non-woven fabric; and laminates having four or more layers such as spunbonded non-woven fabric (ultrafine fiber)/crimped conjugated fiber non-woven fabric/meltblown non-woven fabric/spunbonded non-woven fabric (ultrafine fiber), spunbonded non-woven fabric (ultrafine fiber)/crimped conjugated fiber non-woven fabric/meltblown non-woven fabric/crimped conjugated fiber non-woven fabric/spunbonded non-woven fabric (ultrafine fiber), crimped conjugated fiber non-woven fabric/spunbonded non-woven fabric (ultrafine fiber)/meltblown non-woven fabric/crimped conjugated fiber non-woven fabric, and crimped conjugated fiber non-woven fabric/spunbonded non-woven fabric (ultrafine fiber)/meltblown non-woven fabric/spunbonded non-woven fabric (ultrafine fiber)/crimped conjugated fiber non-woven fabric. The basis weight of each non-woven fabric layer in the laminate is preferably in the range of 2 to 25 g/m². The spunbonded non-woven fabric made of the ultrafine fibers described above may be obtained by controlling (selecting) spunbonding conditions. The non-woven fabric laminates benefit from the bulkiness and softness of the crimped conjugated fiber non-woven fabric of the present invention and also achieve excellent surface smoothness and improved water resistance.

The films laminated with the crimped conjugated fiber non-woven fabric of the present invention are preferably breathable (moisture permeable) films in order to take advantage of the breathability of the crimped conjugated fiber non-woven fabric. Various known breathable films may be used, with examples including films of moisture permeable thermoplastic elastomers such as polyurethane elastomers, polyester elastomers and polyamide elastomers; and porous films obtained by stretching thermoplastic resin films containing inorganic or organic fine particles to create pores in the films. Preferred thermoplastic resins for the porous films are high-pressure low-density polyethylenes, linear low-density polyethylenes (LLDPE), high-density polyethylenes, polypropylenes, polypropylene random copolymers and compositions containing these polyolefins.

The laminates with the breathable films are cloth-like composite materials having bulkiness and softness of the crimped conjugated fiber non-woven fabric of the present invention and very high water resistance.

<Process for Producing Non-Woven Fabric>

The non-woven fabric of the present invention may be produced by any known process while still achieving the advantageous effects of the present invention. A preferred production process is described below.

The non-woven fabric of the present invention is preferably produced through:

(1) a step in which compositions prepared by adding a predetermined amount of the fatty acid amide to the olefin polymer (A) and/or the olefin polymer (B) that are raw materials for the portion (a) and the portion (b) respectively are separately molten in at least two extruders and are spun from a composite spinning nozzle into conjugated fibers;

(2) a step in which the conjugated fibers are quenched, then drawn and attenuated to develop crimps, and the crimped conjugated fibers are deposited on a collecting belt to a desired thickness; and (3) a step in which the deposited conjugated fibers are entangled.

This process is called a spunbonding process.

Step (1)

In this step, known extruders and composite spinning nozzles may be used. The melting temperature is not particularly limited but is preferably higher by approximately 50° C. than the melting point of the olefin polymer. The spinnability in this step is evaluated based on the presence or absence of fiber breakage within a predetermined time.

Step (2)

In this step, the molten fibers are preferably quenched by blowing air. The air temperature may be 10 to 40° C. The quenched fibers may be controlled to a desired diameter by the tensile force of blowing air. The quenched fibers develop crimps. The collecting belt may be conventional but is preferably one that is capable of conveying the crimped fibers, for example a belt conveyer.

Step (3)

The entanglement treatment in this step may be performed for example by applying water jet or ultrasonic wave to the deposited crimped conjugated fibers (hereinafter, also referred to simply as "fibers") or by thermally fusion bonding the fibers by embossing or hot air.

In the present invention, it is particularly preferable that the crimped conjugated fibers are embossed, whereby a non-woven fabric having excellent strength is obtained. The embossing is carried out under conditions such that the embossed area percentage is 3 to 30%. The embossed area percentage represents the total area of emboss relative to the total area of the non-woven fabric. Reducing the embossed area provides a non-woven fabric with excellent softness. Increasing the embossed area gives a non-woven fabric having excellent rigidity and mechanical strength.

The embossing temperature is preferably controlled depending on the melting points of the portions (a) and (b). For the propylene polymer, the embossing temperature is usually in the range of 100 to 150° C.

EXAMPLES

The present invention will be described in greater detail by examples hereinbelow without limiting the scope of the invention.

The propylene polymers used in Examples and Comparative Examples of the present invention are listed below.

(1) Propylene polymer (A) [propylene homopolymer]
Prime Polypro 5119 manufactured by Prime Polymer Co., Ltd.; melting point: 156° C., MFR: 62 g/10 min, Mw/Mn: 2.92, Mz/Mw: 2.35 (A2-1).

(2) Propylene/α-olefin random copolymer (B) [propylene/ethylene random copolymer]
Prime Polypro S229R manufactured by Prime Polymer Co., Ltd.; melting point: 143° C., MFR: 62 g/10 min, Mw/Mn: 2.50, Mz/Mw: 2.10, ethylene content: 3.0% by weight (4.5 mol %) (B2-1).

(3) Propylene polymer (A) [propylene homopolymer]
NOVATEC PP SA06A manufactured by Japan Polypropylene Corporation; melting point: 167° C., MFR: 60 g/10 min, Mw/Mn: 2.92, Mz/Mw: 2.33 (A2-2).

The physical properties of the crimped conjugated continuous fibers and non-woven fabric obtained in Examples and Comparative Examples of the present invention were measured by the following methods.

(1) Number of Crimps

The number of crimps was measured in accordance with JIS L 1015.

(2) KOSHI Value

Measurement in each of tensile, shearing, compression, surface friction and bending tests was carried out on knit high-sensitivity conditions as measurement conditions by KES-FB System manufactured by Kato tech Co., Ltd. The measurement results were obtained as KOSHI values by measurement on knit underwear (summer) conditions. A lower KOSHI value exhibits superior softness.

(3) SHARI Value

Measurement in each of tensile, shearing, compression, surface friction and bending tests was carried out on knit high-sensitivity conditions as measurement conditions by KES-FB System manufactured by Kato tech Co., Ltd. The measurement results were obtained as SHARI values by measurement on knit underwear (summer) conditions. A lower SHARI value exhibits superior surface smoothness and softness.

(4) FUKURAMI Value <Evaluation of Bulkiness>

Measurement in each of tensile, shearing, compression, surface friction and bending tests was carried out on knit high-sensitivity conditions as measurement conditions by KES-FB System manufactured by Kato tech Co., Ltd. The measurement results were obtained as FUKURAMI values by measurement on knit underwear (summer) conditions. A higher FUKURAMI value exhibits a larger thickness and superior softness.

(5) Sensory Evaluation <Index of Softness>

Using samples of 20 cm per side of obtained non-woven fabrics, sensory evaluation for softness was carried out by seven persons in total of four women and three men in a thermostatic chamber at 25° C. The evaluation was made such that each person randomly touched each sample and graded each sample based on a scale of 10, and the average value of the scores of each sample by the seven persons was calculated (the figures after the decimal fractions are omitted). The way of the touching by each person was left to the judgment of the person. A sample with a higher score was determined to be superior in softness.

(6) Fuzz Evaluation

The fuzz weights per unit area ($cm^2$) of the obtained non-woven fabrics were measured by the following method. A smaller fuzz weight indicates a smaller amount of generated fuzz, which is better.

<Measurement Instruments and Accessories>

1) Ink Rud Tester (Danilee Co)
2) Double coated tape: ST-416P (50 mm×30 m), Sumitomo 3M Limited, 3187C
3) Acrylic pressure sensitive adhesive tape (single coated tape: Scotch® surface protection tape manufactured by Sumitomo 3M Limited)
4) Sandpaper: 320 grids (brown), width: 2 inches
5) Weight: dimension; 5×15×3.5 cm, weight; 2200 g <Evaluation Procedure>

1) Double coated tapes of about 15 mm in length are stuck on the non-measuring surface of a sample in MD and CD directions.
2) The sample is cut into a size of 4 cm×11 cm.
3) Two single coated pressure sensitive adhesive tapes of about 19 cm are prepared.
4) The single coated pressure sensitive adhesive tapes are cut, followed by being stuck on release paper of 14×15 cm.
5) The measuring device is provided with the sandpaper and is started to accomplish 43 to-and-fro movements per minute of the sandpaper after setting a counter at 20.
6) The sandpaper is detached to remove fuzz with one single coated pressure sensitive adhesive tape.
7) The other tape is put on the test piece and the weight is put thereon for 20 seconds.
8) The weight of the fuzz before and after the adhesion of the fuzz is measured, and a fuzz weight per unit area ($cm^2$) is measured.

(7) Uniformity Index Evaluation

The average value of the uniformity indices (n=5) of the obtained non-woven fabrics was obtained as a uniformity index value using a formation tester FMT-MIII manufactured by NOMURA SHOJI CO., LTD. A lower uniformity index value indicates better uniformity.

A uniformity index (V) is represented by $V=10\sigma/E$. $\sigma$ is the standard deviation of the inconsistencies in density of a non-woven fabric, and E is obtained by measuring the light transmittance (T) of the non-woven fabric. E is represented by $E=2-\log T$, and when the transmittance is almost 100% (poor uniformity), $E\approx 0$ is established and V indicates an infinitely large value.

(8) Visibility Evaluation

Samples of 20 cm per side of the obtained non-woven fabrics were put on black paper and visibility evaluation for the samples was carried out by seven persons in total of four women and three men in a thermostatic chamber at 25° C. The evaluation was made such that each person graded each sample based on a scale of 5, and the average value of the scores of each sample by the seven persons was calculated (the figures after the decimal fractions are omitted). The way of looking by each person was left to the judgment of the person. A sample with a higher score was determined to be superior in visibility.

Example 1

A composition prepared by adding 1 part by weight of stearic acid amide to 100 parts by weight of A2-1 described above was used in a core, while a composition prepared by adding 1 part by weight of stearic acid amide to 100 parts by weight of B2-1 described above was used in a sheath. The compositions were melt-spun by spunbonding method.

Single-screw extruders were used and the compositions were molten at 200° C.

The compositions were spun into continuous fibers in which the mass ratio of a core h1 to a sheath h2 was 20:80. In this case, the fiber rate was 2060 m/min and the fineness was 2.3 denier.

The resultant eccentric core-sheath crimped conjugated continuous fibers that were melt-spun were deposited on a collecting surface to form a non-woven fabric. The non-woven fabric was embossed at 125° C. by quilt embossment. The embossed area percentage was 9.7%. The embossed non-woven fabric had a basis weight of 25 g/m$^2$. The resultant crimped conjugated continuous fibers and non-woven fabric were evaluated for properties by the above-described methods.

The measurement results are set forth in Table 1.

Example 2

Crimped conjugated continuous fibers and a non-woven fabric were obtained in the same manner as in Example 1, except that the compositions used in Example 1 were changed to compositions prepared by adding 1 part by weight of oleic acid amide to 100 parts by weight of A2-1 and B2-1, respectively. The measurement results for the crimped conjugated continuous fibers and the non-woven fabric are set forth in Table 1.

Example 3

Crimped conjugated continuous fibers and a non-woven fabric were obtained in the same manner as in Example 1, except that the compositions used in Example 1 were changed to compositions prepared by adding 1 part by weight of N-oleylpalmitic acid amide to 100 parts by weight of A2-1 and B2-1, respectively. The measurement results for the crimped conjugated continuous fibers and the non-woven fabric are set forth in Table 1.

Comparative Example 1

Crimped conjugated continuous fibers and a non-woven fabric were obtained in the same manner as in Example 1, except that the compositions used in Example 1 were changed to A2-1 and B2-1 neither of which contained fatty acid amide. The measurement results for the crimped conjugated continuous fibers and the non-woven fabric are set forth in Table 1.

Comparative Example 2

Crimped conjugated continuous fibers and a non-woven fabric were obtained in the same manner as in Example 1, except that the compositions used in Example 1 were changed to compositions prepared by adding 1 part by weight of erucic acid amide to 100 parts by weight of A2-1 and B2-1, respectively. The measurement results for the crimped conjugated continuous fibers and the non-woven fabric are set forth in Table 1.

Comparative Example 3

Crimped conjugated continuous fibers and a non-woven fabric were obtained in the same manner as in Example 1, except that the compositions used in Example 1 were changed to A2-2 which contained no fatty acid amide for a core and B2-1 which contained no fatty acid amide for a sheath. The measurement results for the crimped conjugated continuous fibers and the non-woven fabric are set forth in Table 1.

TABLE 1

|  |  |  | Examples | | | Comparative Examples | | |
|---|---|---|---|---|---|---|---|---|
|  |  |  | Example 1 | Example 2 | Example 3 | Comparative Example 1 | Comparative Example 2 | Comparative Example 3 |
| Additive | Type of additive | | Stearic acid amide | Oleic acid amide | Oleylpalmitic acid amide | None | Erucic acid amide | None |
|  | Amount of additive | Part by weight | 1.0 | 1.0 | 1.0 | 0.0 | 1.0 | 0.0 |
| Production conditions | Fiber bonding method (embossment type) | | Quilt | Quilt | Quilt | Quilt | Quilt | Quilt |
|  | Bonded (embossed) area percentage | | 9.7 | 9.7 | 9.7 | 9.7 | 9.7 | 9.7 |
| Polymers (A) and (B) | Difference between melting points | °C. | 13 | 13 | 13 | 13 | 13 | 24 |
|  | MFR | Polymer (A) | 62 | 62 | 62 | 62 | 62 | 60 |
|  |  | Polymer (B) | 62 | 62 | 62 | 62 | 62 | 62 |
|  | $\Delta Mz/Mw$ | — | 0.25 | 0.25 | 0.25 | 0.25 | 0.25 | 0.23 |
| Conjugated fibers | Resin configuration | | h-PP/r-PP | h-PP/r-PP | h-PP/r-PP | h-PP/r-PP | h-PP/r-PP | h-PP/r-PP |
| Non-woven fabric | Basis weight | g/m$^2$ | 25 | 25 | 25 | 25 | 25 | 25 |
| Properties | Number of crimps | crimps/25 mm | 23.1 | 20.6 | 23.5 | 15.0 | 17.5 | 60.0 |
|  | Softness evaluation | KOSHI | 6.68 | 7.34 | 7.03 | 7.53 | 7.94 | 7.44 |
|  |  | SHARI | −1.69 | −1.04 | −1.69 | −0.96 | −0.24 | −0.92 |
|  | KES | FUKURAMI | 11.34 | 11.93 | 11.73 | 10.35 | 8.51 | 10.86 |
|  | Sensory evaluation | Score | 8 | 8 | 8 | 6 | 6 | 7 |
|  | Fuzz evaluation | g/cm$^2$ | 0.07 | 0.05 | 0.06 | 0.16 | 0.12 | 0.20 |
|  | Uniformity index | — | 358 | 315 | 344 | 463 | 432 | 585 |
|  | Visibility | | 4 | 4 | 4 | 2 | 2 | 1 |

INDUSTRIAL APPLICABILITY

The non-woven fabric according to the present invention has excellent properties such as spinnability, strength, softness and water resistance and is useful in side gathers, back sheets, top sheets and waist parts of disposable diapers or sanitary napkins.

REFERENCE SIGNS LIST

10 . . . portion (a)
20 . . . portion (b)

The invention claimed is:

1. A crimped conjugated fiber having a crimpable cross-sectional configuration, wherein a cross section of the fiber comprises at least two portions: a portion (a) and a portion (b); the mass ratio of the portion (a) to the portion (b) [(a):(b)] is in the range of 10:90 to 60:40; the portion (a) comprises an olefin polymer (A) and the portion (b) comprises an olefin polymer (B); the olefin polymer (A) differs from the olefin polymer (B) in at least any one of Mz/Mw (a ratio of Z-average molecular weight (Mz) to weight average molecular weight (Mw)), melting point and MFR (melt flow rate); and a fatty acid amide having 19 or less carbon atoms is added to the olefin polymer (A) and/or the olefin polymer (B);
wherein the difference between the melting points of the olefin polymer (A) and the olefin polymer (B) is less than 20° C., and the blended amount of the fatty acid amide having 19 or less carbon atoms is in the range of 0.1 to 10 parts by weight based on 100 parts by weight of the olefin polymer (A) and/or the olefin polymer (B).

2. The crimped conjugated fiber according to claim 1, wherein the crimped conjugated fiber has an eccentric core-sheath configuration in which the portion (a) is a core (a') and the portion (b) is a sheath (b').

3. The crimped conjugated fiber according to claim 1, wherein the olefin polymer (A) and the olefin polymer (B) are a propylene polymer (A1) and a propylene polymer (B1), respectively.

4. The crimped conjugated fiber according to claim 3, wherein the propylene polymer (A1) and the propylene polymer (B1) are a propylene homopolymer (A2) and a propylene/α-olefin copolymer (B2), respectively.

5. The crimped conjugated fiber according to claim 1, wherein the fatty acid amide is stearic acid amide, oleic acid amide, or oleylpalmitic acid amide.

6. A non-woven fabric comprising the crimped conjugated fiber according to claim 1.

7. A non-woven fabric laminate comprising a layer configuration including at least two or more layers, wherein at least one layer of the two or more layers is the non-woven fabric according to claim 6.

8. An absorbent article comprising the non-woven fabric according to claim 6, wherein the non-woven fabric is used in a top sheet and/or a second sheet.

9. An absorbent article comprising the non-woven fabric according to claim 6, wherein the non-woven fabric is used in a sheet in which an absorber is wrapped.

10. The crimped conjugated fiber according to claim 1, wherein the difference between the melting points of the olefin polymer (A) and the olefin polymer (B) is more than 10° C.

* * * * *